United States Patent
Burbank et al.

(10) Patent No.: US 8,641,615 B2
(45) Date of Patent: Feb. 4, 2014

(54) METHOD AND APPARATUS FOR MACHINE ERROR DETECTION BY COMBINING MULTIPLE SENSOR INPUTS

(71) Applicant: NXStage Medical, Inc., Lawrence, MA (US)

(72) Inventors: Jeffrey H. Burbank, Boxford, MA (US); James M. Brugger, Newburyport, MA (US)

(73) Assignee: NXstage Medical, Inc., Lawrence, MA (US)

( * ) Notice: Subject to any disclaimer, the term of this patent is extended or adjusted under 35 U.S.C. 154(b) by 0 days.

(21) Appl. No.: 13/921,115

(22) Filed: Jun. 18, 2013

(65) Prior Publication Data
US 2013/0281799 A1    Oct. 24, 2013

Related U.S. Application Data

(63) Continuation of application No. 13/406,332, filed on Feb. 27, 2012, which is a continuation of application No. 10/037,254, filed on Jan. 4, 2002, now abandoned.

(51) Int. Cl.
| | |
|---|---|
| A61B 5/00 | (2006.01) |
| A61M 1/10 | (2006.01) |
| A61M 1/14 | (2006.01) |
| A61M 1/36 | (2006.01) |
| A61M 1/16 | (2006.01) |
| G06F 19/00 | (2011.01) |
| G08B 21/02 | (2006.01) |
| G06K 9/62 | (2006.01) |
| G06Q 50/22 | (2012.01) |

(52) U.S. Cl.
CPC . *A61M 1/10* (2013.01); *A61M 1/14* (2013.01); *A61M 1/3621* (2013.01); *A61M 1/1692* (2013.01); *G06F 19/3406* (2013.01); *G06F 19/345* (2013.01); *G06Q 50/22* (2013.01); *G08B 21/02* (2013.01); *G08B 21/0211* (2013.01); *G06K 9/62* (2013.01); *G06K 9/6228* (2013.01); *G06K 9/6278* (2013.01)
USPC ...... 600/300; 210/645; 340/539.12; 340/522; 702/19; 706/20; 706/21; 604/5.01

(58) Field of Classification Search
None
See application file for complete search history.

(56) References Cited

U.S. PATENT DOCUMENTS

| | | |
|---|---|---|
| 3,744,524 A | 7/1973 | Blau |
| 3,864,676 A | 2/1975 | Macias et al. |

(Continued)

FOREIGN PATENT DOCUMENTS

| | | |
|---|---|---|
| CN | 202154895 | 3/2010 |
| DE | 1964735 | 7/1971 |

(Continued)

OTHER PUBLICATIONS

NPL_Sensor terminology_2010, p. 1-5.

(Continued)

*Primary Examiner* — Bill Thomson
*Assistant Examiner* — Marie Archer
(74) *Attorney, Agent, or Firm* — Miles & Stockbridge P.C.; Mark A. Catan

(57) ABSTRACT

One of the most significant safety concerns in the automation of extracorporeal blood treatments such as dialysis is the risk of blood leakage. Extracorporeal blood treatment systems draw blood at such a high rate that a loss of integrity in the blood circuit can be serious. There are a number of mechanisms for detecting and preventing leaks, but none is perfect. This tends to limit the use of such equipment in unsupervised settings, such as the home will be limited. Some leak detection schemes can be made sensitive enough to detect the barest of leaks, but when this is done, they result in too many false positives. The invention combines information from multiple inputs to enhance sensitivity in leak detection and reduce the problem of false positives.

2 Claims, 8 Drawing Sheets

(56) References Cited

U.S. PATENT DOCUMENTS

| | | | |
|---|---|---|---|
| 3,985,134 | A | 10/1976 | Lissot et al. |
| 4,083,777 | A | 4/1978 | Hutchisson |
| 4,181,610 | A | 1/1980 | Shintani et al. |
| 4,364,261 | A | 12/1982 | Askwith et al. |
| 4,507,114 | A | 3/1985 | Bohman et al. |
| 4,610,665 | A | 9/1986 | Matsumoto et al. |
| 4,614,590 | A | 9/1986 | Rath et al. |
| 4,954,149 | A | 9/1990 | Fullemann |
| 5,041,097 | A | 8/1991 | Johnson |
| 5,120,303 | A | 6/1992 | Hombrouckx |
| 5,361,379 | A * | 11/1994 | White ............................ 382/227 |
| 5,368,555 | A | 11/1994 | Sussman et al. |
| 5,394,732 | A | 3/1995 | Johnson et al. |
| 5,486,286 | A | 1/1996 | Peterson et al. |
| 5,515,713 | A | 5/1996 | Saugues et al. |
| 5,624,551 | A | 4/1997 | Baumann et al. |
| 5,687,764 | A | 11/1997 | Tanaka et al. |
| 5,690,831 | A | 11/1997 | Kenley et al. |
| 5,744,027 | A | 4/1998 | Connell et al. |
| 5,910,252 | A | 6/1999 | Truitt et al. |
| 6,044,691 | A | 4/2000 | Kenley et al. |
| 6,066,261 | A | 5/2000 | Spickermann |
| 6,080,321 | A | 6/2000 | Spickermann |
| 6,090,048 | A | 7/2000 | Hertz et al. |
| 6,177,049 | B1 | 1/2001 | Schnell et al. |
| 6,187,207 | B1 | 2/2001 | Brauer |
| 6,221,040 | B1 | 4/2001 | Kleinekofort |
| 6,228,271 | B1 | 5/2001 | Cote |
| 6,269,679 | B1 | 8/2001 | McCarthy et al. |
| 6,280,632 | B1 | 8/2001 | Polaschegg |
| 6,284,142 | B1 | 9/2001 | Muller |
| 6,308,737 | B1 | 10/2001 | Kritiviski et al. |
| 6,327,895 | B1 | 12/2001 | Jeppsson et al. |
| 6,332,100 | B1 | 12/2001 | Sahai et al. |
| 6,401,518 | B1 | 6/2002 | O'Keeffe et al. |
| 6,423,022 | B1 | 7/2002 | Roeher et al. |
| 6,461,329 | B1 | 10/2002 | Van Antwerp et al. |
| 6,530,262 | B1 | 3/2003 | Esser |
| 6,572,576 | B2 | 6/2003 | Brugger et al. |
| 6,585,675 | B1 | 7/2003 | O'Mahony et al. |
| 6,609,036 | B1 | 8/2003 | Bickford |
| 6,611,206 | B2 | 8/2003 | Milanski et al. |
| 6,780,322 | B1 | 8/2004 | Bissler et al. |
| 6,804,991 | B2 | 10/2004 | Balschat et al. |
| 6,846,161 | B2 | 1/2005 | Kline et al. |
| 7,040,142 | B2 | 5/2006 | Burbank |
| 7,096,125 | B2 | 8/2006 | Padmanabhan et al. |
| 7,605,710 | B2 | 10/2009 | Crnkovich et al. |
| 7,755,488 | B2 | 7/2010 | Dvorsky |
| 8,017,826 | B2 | 9/2011 | Utterberg et al. |
| 8,048,045 | B2 | 11/2011 | Engvall |
| 8,083,677 | B2 | 12/2011 | Rohde |
| 2001/0039441 | A1 | 11/2001 | Ash |
| 2002/0085952 | A1 | 7/2002 | Ellingboe et al. |
| 2003/0128125 | A1 | 7/2003 | Burbank et al. |
| 2003/0128126 | A1 | 7/2003 | Burbank et al. |
| 2004/0186415 | A1 | 9/2004 | Burbank et al. |
| 2007/0010779 | A1 | 1/2007 | Utterberg et al. |
| 2007/0293748 | A1 | 12/2007 | Engvall et al. |
| 2009/0082646 | A1 | 3/2009 | Bouton |
| 2009/0082676 | A1 | 3/2009 | Bennison |
| 2009/0212178 | A1 | 8/2009 | Westberg |
| 2010/0100026 | A1 | 4/2010 | Morris |
| 2010/0140149 | A1 | 6/2010 | Fulkerson et al. |
| 2010/0294286 | A1 | 11/2010 | Bellamy et al. |
| 2011/0071367 | A1 | 3/2011 | Court et al. |
| 2011/0071467 | A1 | 3/2011 | Court et al. |
| 2011/0184329 | A1 | 7/2011 | Kramer et al. |

FOREIGN PATENT DOCUMENTS

| | | |
|---|---|---|
| DE | 3209845 | 9/1983 |
| EP | 2420219 | 2/2012 |
| IN | 2011DN02879 | 3/2012 |
| JP | 2010172419 | 8/2010 |
| WO | WO 99/24145 | 5/1999 |
| WO | WO 03/006944 | 1/2003 |
| WO | WO 03/058567 | 7/2003 |
| WO | WO 03/058608 | 7/2003 |
| WO | WO 2004/084972 | 10/2004 |
| WO | WO 2005/046439 | 5/2005 |

OTHER PUBLICATIONS

Bunn, D.W., "Bayesian approach to the Linear combination of Forecasts", Opl Res. Q., Pergamon Press 1975. vol. 26, I, pp. 325 to 329.
Heckermann, D., "A tutorial on Learning with Bayesian Networks", Technical Report, 1995, Microsoft research, p. 1-58.

* cited by examiner

METHOD AND APPARATUS FOR MACHINE ERROR DETECTION BY COMBINING MULTIPLE SENSOR INPUTS

FIELD OF THE INVENTION

The present invention relates to the detection of leaks (including needle-disconnects and other causes of loss of integrity) in extracorporeal blood circuits and more particularly to the use of multiple input types to determine if a leak condition exists.

BACKGROUND

Many medical procedures involve the extraction and replacement of flowing blood from, and back into, a donor or patient. The reasons for doing this vary, but generally, they involve subjecting the blood to some process that cannot be carried out inside the body. When the blood is outside the patient it is conducted through machinery that processes the blood. The various processes include, but are not limited to, hemodialysis, hemofiltration, hemodiafiltration, blood and blood component collection, plasmaphresis, aphresis, and blood oxygenation.

One technique for extracorporeal blood processing employs a single "access," for example a single needle in the vein of the patient or a fistula. A volume of blood is cyclically drawn through the access at one time, processed, and then returned through the same access at another time. Single access systems are uncommon because they limit the rate of processing to half the capacity permitted by the access. As a result, two-access systems, in which blood is drawn from a first access, called an arterial access, and returned through a second access, called a venous access, are much faster and more common. These accesses include catheters, catheters with subcutaneous ports, fistulas, and grafts.

The processes listed above, and others, often involve the movement of large amounts of blood at a very high rate. For example, 500 ml. of blood may be drawn out and replaced every minute, which is about 5% of the patient's entire supply. If a leak occurs in such a system, the patient could be drained of enough blood in a few minutes to cause loss of consciousness with death following soon thereafter. As a result, such extracorporeal blood circuits are normally used in very safe environments, such as hospitals and treatment centers, and attended by highly trained technicians and doctors nearby. Even with close supervision, a number of deaths occur in the United States every year due to undue blood loss from leaks.

Leaks present a very real risk. Leaks can occur for various reasons, among them: extraction of a needle, disconnection of a luer, poor manufacture of components, cuts in tubing, and leaks in a catheter. However, in terms of current technology, the most reliable solution to this risk, that of direct and constant trained supervision in a safe environment, has an enormous negative impact on the lifestyles of patients who require frequent treatment and on labor requirements of the institutions performing such therapies. Thus, there is a perennial need in the art for ultra-safe systems that can be used in a non-clinical setting and/or without the need for highly trained and expensive staff. Currently, there is great interest in ways of providing systems for patients to use at home. One of the risks for such systems is the danger of leaks. As a result, a number of companies have dedicated resources to the solution of the problem of leak detection.

In single-access systems, loss of blood through the patient access and blood circuit can be indirectly detected by detecting the infiltration of air during the draw cycle. Air is typically detected using an ultrasonic air detector on the tubing line, which detects air bubbles in the blood. The detection of air bubbles triggers the system to halt the pump and clamp the line to prevent air bubbles from being injected into the patient. Examples of such systems are described in U.S. Pat. Nos. 3,985,134, 4,614,590, and 5,120,303.

While detection of air infiltration is a reliable technique for detecting leaks in single access systems, the more attractive two-access systems, in which blood is drawn continuously from one access and returned continuously through another, present problems. While a disconnection or leak in the draw line can be sensed by detecting air infiltration, just as with the single needle system, a leak in the return line cannot be so detected. This problem has been addressed in a number of different ways, some of which are generally accepted in the industry.

The first level of protection against return line blood loss is the use of locking luers on all connections, as described in International Standard ISO 594-2 which help to minimize the possibility of spontaneous disconnection during treatment. Care in the connection and taping of lines to the patient's bodies is also a known strategy for minimizing this risk.

A higher level of protection is the provision of venous pressure monitoring, which detects a precipitous decrease in the venous line pressure. This technique is outlined in International Standard IEC 60601-2-16. This approach, although providing some additional protection, is not very robust, because most of the pressure loss in the venous line is in the needle used to access the patient. There is very little pressure change in the venous return line that can be detected in the event of a disconnection, so long as the needle remains attached to the return line. Thus, the pressure signal is very weak. The signal is no stronger for small leaks in the return line, where the pressure changes are too small to be detected with any reliability. One way to compensate for the low pressure signal is to make the system more sensitive, as described in U.S. Pat. No. 6,221,040, but this strategy can cause many false positives. It is inevitable that the sensitivity of the system will have to be traded against the burden of monitoring false alarms. Inevitably this leads to compromises in safety. In addition, pressure sensing methods cannot be used at all for detecting small leaks.

Yet another approach, described for example in PCT application US98/19266, is to place fluid detectors near the patient's access and/or on the floor under the patient. The system responds only after blood has leaked and collected in the vicinity of a fluid detector. A misplaced detector can defeat such a system and the path of a leak cannot be reliably predicted. For instance, a rivulet of blood may adhere to the patient's body and transfer blood to points remote from the detector. Even efforts to avoid this situation can be defeated by movement of the patient, deliberate or inadvertent (e.g., the unconscious movement of a sleeping patient).

Still another device for detecting leaks is described in U.S. Pat. No. 6,044,691. According to the description, the circuit is checked for leaks prior to the treatment operation. For example, a heated fluid may be run through the circuit and its leakage detected by means of a thermistor. The weakness of this approach is immediately apparent: there is no assurance that the system's integrity will persist, throughout the treatment cycle, as confirmed by the pre-treatment test. Thus, this method also fails to address the entire risk.

Yet another device for checking for leaks in return lines is described in U.S. Pat. No. 6,090,048. In the disclosed system, a pressure signal is sensed at the access and used to infer its integrity. The pressure wave may be the patient's pulse or it may be artificially generated by the pump. This approach cannot detect small leaks and is not very sensitive unless powerful pressure waves are used; in which case the effect can produce considerable discomfort in the patient.

Clearly detection of leaks by prior art methods fails to reduce the risk of dangerous blood loss to an acceptable level. In general, the risk of leakage-related deaths increases with the decrease in medical staff per patient driven by the high cost of trained staff. Currently, with lower staffing levels comes the increased risk of unattended leaks. Thus, there has been, and continues to be, a need in the prior art for a fool-proof approach to detection of a return line leak or disconnection.

In an area unrelated to leak detection, U.S. Pat. No. 6,177, 049 B1 suggests the idea of reversing the direction of blood flow for purposes of patency testing and access-clearing. The patency tests alluded to by the '049 patent refer simply to the conventional idea of forcing blood through each access to clear occlusions and to ascertain the flow inside a fistula.

SUMMARY OF THE INVENTION

Leaks can be detected in a number of ways, but no leak detection device is perfect. According to the present invention, the inputs of multiple leak detection devices are combined to increase sensitivity and reduce false alarms. According to an embodiment of the invention, status signals from various different sources, some of which may be only weakly determinative of a leak or other alarm condition, are combined to provide a robust signal indicative of patient or equipment status. The increase in reliability is extremely important due to the risks in the use of such equipment as extracorporeal blood processing systems.

Among the various sensor inputs are:
1. gauge pressure of the line upstream and/or downstream of patient access, which is known to be a useful indicator of a disconnection of a luer;
2. pressure drop over a portion of a blood circuit, a leak or disconnection across which would produce a change in pressure drop over that portion of the circuit;
3. patient pulse sensed by a pressure monitor of a line connected to patient access, for example, the pulse pressure sensed at a patient access, which becomes faster and weaker as patient loses blood volume;
4. patient's total body weight, which will drop if blood is lost;
5. blood oxygen, which
6. air sensors, which are normally located along the blood circuit to detect infiltration of air due to a leak or disconnect;
7. fluid sensors located to detect blood flowing from a leak into the open environment;
8. patient heart rate, which rises as blood volume drops;
9. skin color monitored by a video camera or some other optical sensor, which may change as blood is lost;
10. continuity detectors connected with the needle to detect the lack of blood wetting continuity terminals resulting from inadvertent extraction of the needle;
11. bioimpedance sensors used in various locations to indicate extraction of a needle or patient tissue change due to blood loss.
12. acoustic sensor located to respond to infiltration of air into blood line, sounds made by the patient, such as breathing or snoring, etc.

The above list is not intended to be comprehensive. Rather it is suggests the diversity of different kinds of data that may be combined to indicate status or alarm conditions.

According to an embodiment of the invention, the various sensor signals are applied to some sort of signal combiner to produce a composite signal that may be used for status or alarm. Linear or non-linear techniques may be used such as network classifiers, Bayesian networks, or fuzzy logic algorithms according to known techniques.

According to a further refinement, the system may be designed to generate multiple alarm levels to indicate the gravity and/or certainty of the alarm condition. The alarm levels may be tied to how long an existing alarm condition has existed without a response, increase in the number of alarm conditions requiring attention, and/or reliability of a probabilistic alarm condition determination.

The invention provides multiple benefits. First, the combination of multiple input signals to generate an alarm allows data that would otherwise be insufficiently reliable by itself to be usable to make a valuable contribution. In other words, any measurement that is prone to generate false positive alarm states can be dangerous because of the possibility of attendants becoming insensitive to the alarm because of its unreliability. Ideally, alarms are sensitive, but reliable. Combining multiple alarm inputs, each of which on its own is unreliable, may produce a probabilistic estimate whose reliability increases with each input component. Thus, a highly reliable alarm system can be generated from individually unreliable signals and a very reliable system can be made even more reliable by augmenting it. From this perspective, a linear combination of independent inputs enhances the signal-to-noise ratio. Of course, weighted sums and non-linear combinations can also enhance the signal-to-noise ratio of a signal as is well known in some areas of signal processing.

Another advantage in combining status signals is that some status information complements other status information. For example, venous pressure monitoring may provide an early indication of a leak. If something were to go wrong with the early stage detection, a later stage detection may be provided by, for example, the patient's weight or heart rate, which would drop due to blood loss.

The multiple-input/multiple-level alarm system of the invention may require many sensors to communicate with a controller and for the controller to communicate with multiple output devices and user interfaces. But, as it happens that, often, the components of a multiple input, multiple-level alarm system may only need to communicate with each when conditions reach an abnormal status. This application, therefore, provides a inoffensive context for using acoustic signals to communicate between components; a sort of "chirp network" to interconnect the functional components of the system. Note that the same functionality may be achieved by generating audio signals outside the range of human hearing or using spread-spectrum techniques to reduce the sound pressure to subaudible levels at any given frequency and reduce the subjective impact of sound.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with

DETAILED DESCRIPTION OF THE EMBODIMENTS

Figure 1A:
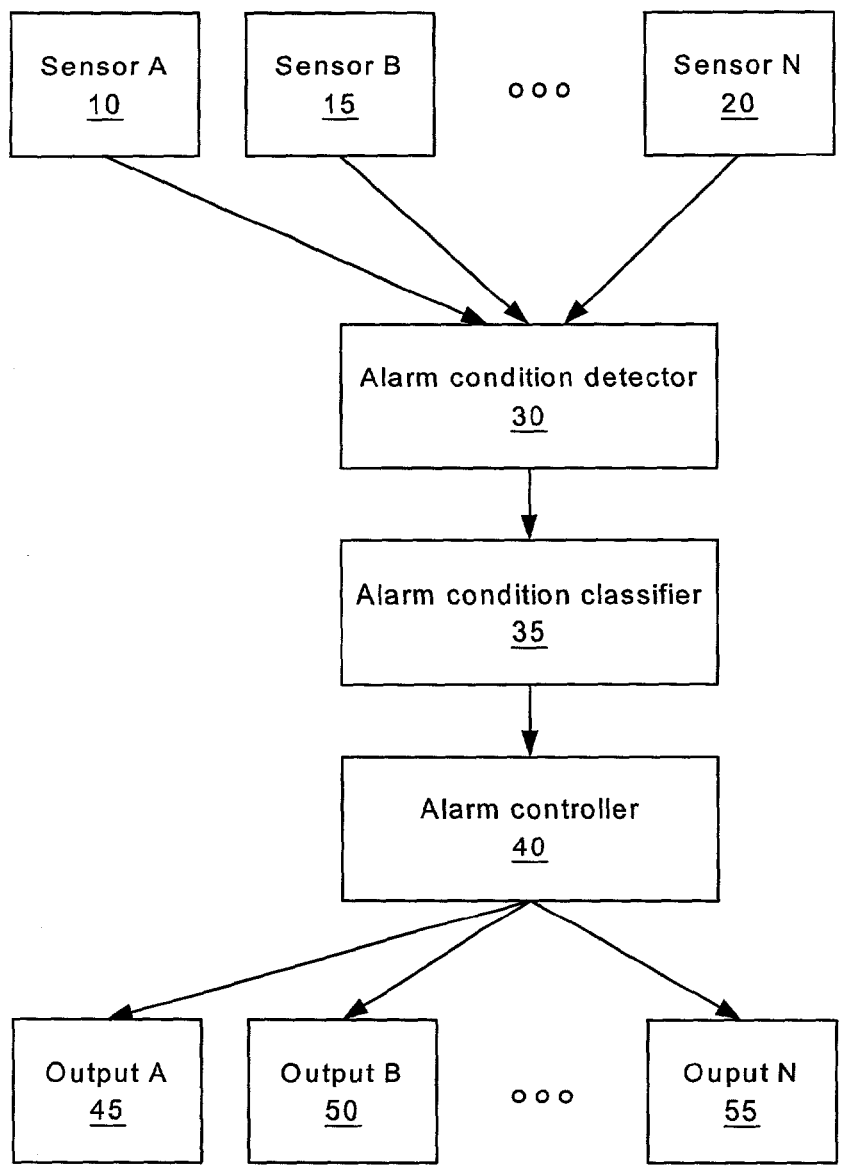
FIG. 1A is an overview block diagram of functional components of a multiple-sensor multiple-level alarm system according to an embodiment of the invention.

Referring to FIG. 1A according to an embodiment of the invention, signals from multiple sensor inputs A, B, . . . N indicated at 10, 15, . . . 20 are applied to an alarm condition detector 30. The alarm condition detector determines whether an alarm condition exists. One of the ideas behind this configuration of combining multiple inputs is that effect that are insufficiently determinative on their own to be reliable alarm indicators can, in combination, provide a highly reliable indicator of an alarm condition. That is, if multiple sensor signals are combined to produce a net valence, the impact of a false positive or negative in any one of them is reduced.

An alarm condition classifier 35 may then identify the nature of the alarm condition detected by the alarm condition detector. The functions of detecting an alarm condition 30 and classifying the alarm condition 35 (i.e. identifying the type of alarm condition) would be performed by the same process or step. For example, in a classification engine such as a Bayesian classifier or neural network, many inputs are combined to "recognize" the current system status. Determining the status, for example: patient has lost a significant amount of blood, could be a classification derived from multiple simultaneous inputs, for example: elevated heart rate, fluid detected outside blood circuit, air detected inside blood circuit, and patient weight dropping slightly. Each of these different inputs contribute to varying degrees and ways depending on the values of other inputs according to how the classifier is programmed. In sophisticated systems that make use of artificial-intelligence, the interaction of the inputs can be complex. But, from the overarching perspective, many inputs are combined to generate a current status signal and that status signal is either a normal status or an aberrant status, the latter being one for which an alarm may be generated. Thus, the process of classifying the status includes detecting an alarm condition.

Put another way, the current state vector is the ordered set of all current values of the sensors 10-20. Classification reduces the large variety of state vectors to some set of state classes some of which correspond to normal and some of which correspond to alarm state classes. The recognition of abnormal state vectors subsumes the step of identifying the class to which the state vector belongs.

Figure 1B:
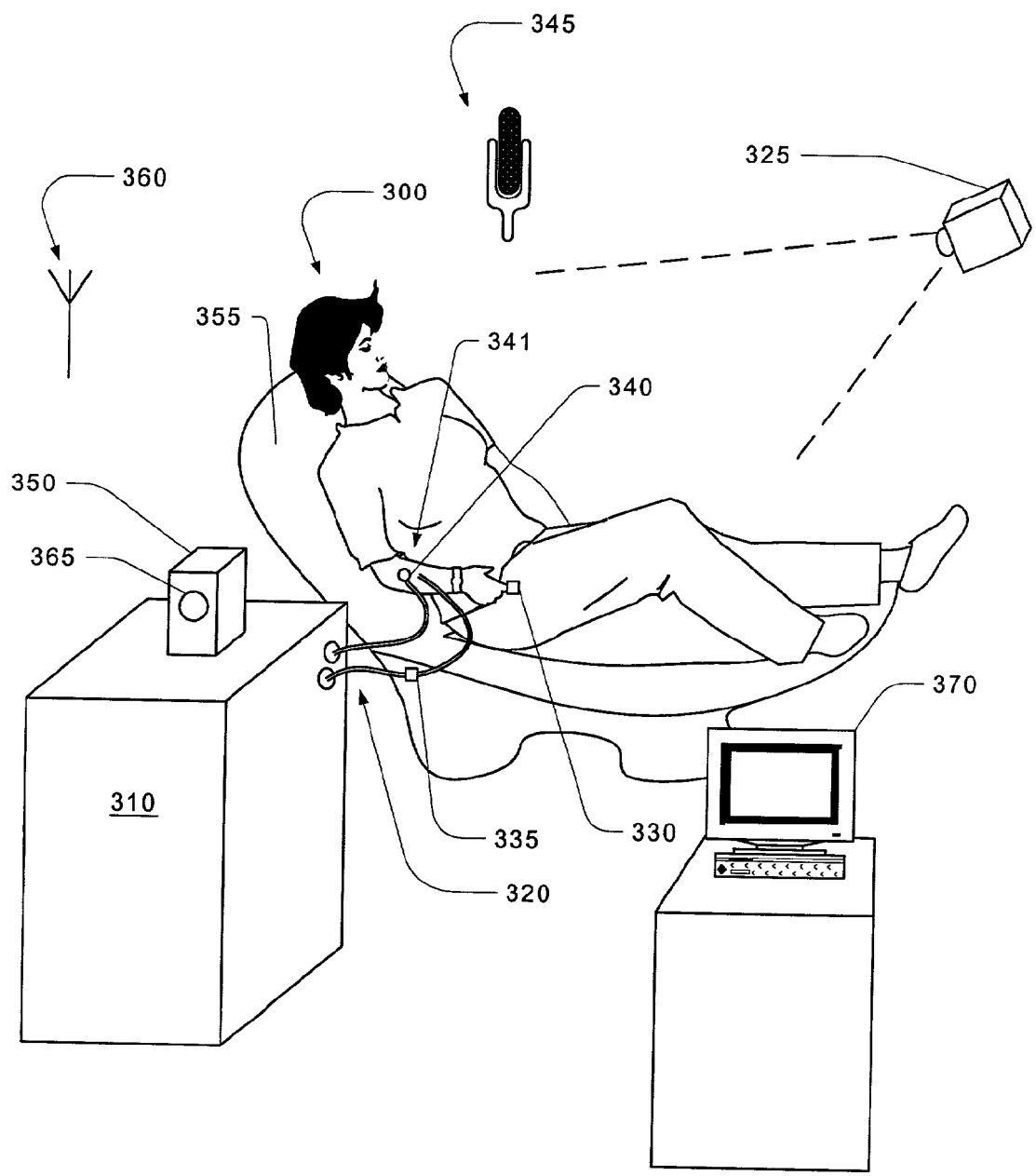
FIG. 1B is a block diagram of an alarm condition detection and control system for a blood treatment device according to an embodiment of the invention and consistent with the embodiment of FIG. 1A.

Referring now to FIG. 1B, to illustrate a hardware environment where the multiple inputs/multiple level alarm system may be used, consider a patient 300 being treated by an extracorporeal blood treatment machine 310. A pressure monitor 340 is connected to monitor a patient access 341. A monitoring system node 350 has an alarm output 365, which may include, for example, a flashing light or a speaker or siren. Not shown here, the alarm output may additionally or alternatively have a component for sending messages via public or private telephone (i.e., private branch exchange, "PBX," or publicly switch telephone networks, "PSTN"), cell networks, computer networks, the Internet, or radio transmissions e.g., as indicated by the antenna 360, to other locations. A video camera 325 continuously captures images of the patient 300 and transmits these to the monitoring system node 350, which may include an image-, or video-, processing component to reduce data in the image or video sequence to some form manageable to be classified in the monitoring system node 350.

Various other sensors may include a pulse monitor, for example a fingertip pulse monitor 330, a blood circuit pressure monitor 335, etc. A user-interface terminal 370 permits alarms to be responded to and for changes to be made in programming, initialization, and training of classification algorithms.

Image and video processing are complex fields where much development activity is occurring. It is possible for image processing software to "recognize" faces, specific objects, certain colors, and various different components of a scene in a field of view. For example, known image processing techniques can be used to zero-in on the face of the patient 300 and to recognize changes in facial expression or body position. These may be classified according to various schemes and used as inputs to the alarm condition detector 30/classifier 35 of FIG. 1A. For an example, a body position output might be the average angle formed by the body at the major joints or the amount of movement of the hands. The facial expression output may be according to a number of published works produced by academic research directed at making user interfaces more responsive to user's current emotional state.

A microphone 345 or other transducer such as a directional sound transducer may capture sounds generated by the patient 300 or other occupants. Front-end processing that may be applied to sound input includes speech recognition and classification of normal and irregular sound patterns.

Figure 1C:
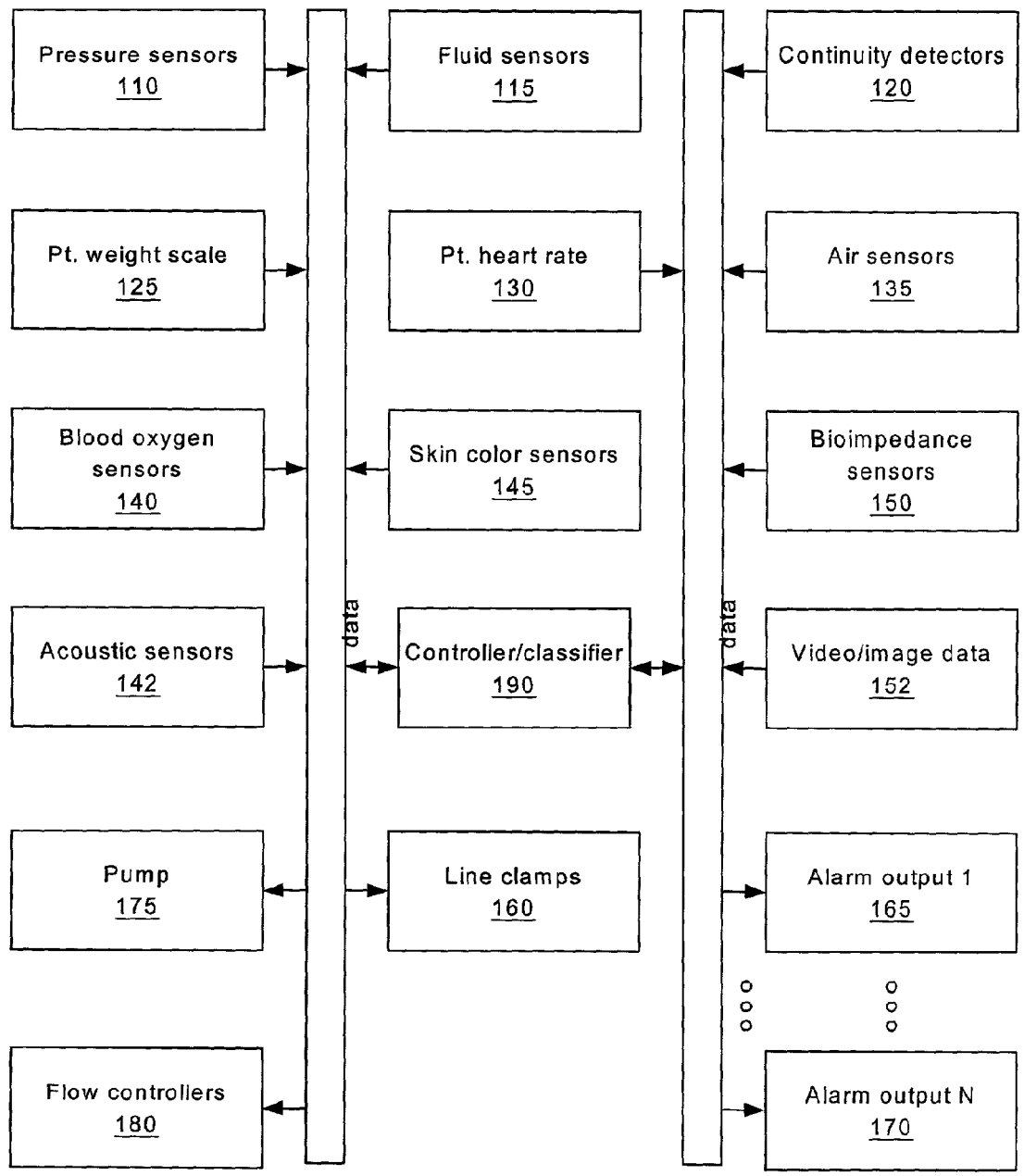
FIG. 1C is a figurative diagram of a hardware context in which the invention may be implemented.

Referring to FIG. 1C, to illustrate some of the kinds of inputs that can be combined to drive an alarm system according to the invention, a controller/classifier 190 receives signals from a plurality of different sensors 110-152 and outputs control signals to various output devices and final controllers 160-180. In an implementation of the invention, any all or different input and output devices may be employed, the illustrated embodiment being an example for purposes of discussion only. The controller/classifier 190 combines the data from the various inputs to determine a current alarm level and takes various actions based on the current alarm level. The input signal may be combined in a linear or non-linear fashion using analog or digital mechanisms for signal processing to generate its output signals. The controller/classifier 190 may be an analog or digital device, but is preferably based on a programmable processor. Also, preferably, it includes a user interface (not shown separately in FIG. 1) for modifying its settings and allowing a user to respond to alarms.

Pressure sensors 110 may be any of a variety of different absolute, gauge, or differential pressure-monitoring sensors that have been proposed for use in leak detection. For example, venous line pressure monitoring as described in International Standard IEC 60601-2-16 and U.S. Pat. No. 6,221,040. The pressure sensors 110 may also be one or more differential pressure monitors, that may be used to test a portion of a circuit by clamping both ends of the portion and observing the gauge pressure for a brief interval for a change that would indicate leakage. See, for example, the discussion attending FIG. 5, below.

A patient weight scale 125 may be used to generate a current weight for the patient. Such a scale 125 may be built into a chair, couch, or bed. The patient weight scale 125 input device may produce a time-integrated signal using a low pass filter (not illustrated) to remove transients due to patient movement. The patient weight by itself may be too subtle a signal, or provide inadequate lead-time to used alone for patient safety, but it may participate in earlier warning if combined with other data and may provide help in late stage warning or alarm escalation as discussed in more detail below, particularly with reference to FIG. 6.

Blood oxygen sensors 140 provide an indication of blood oxygen level, which may indicate blood loss due to a leak. Blood oxygen sensors 140 may be optical-based sensors and may be located along the blood circuit.

Acoustic sensors 142 may be used to advantage in leak detection in a number of ways. In the commonly-assigned application incorporated by reference below, audio sensors 142 are proposed as a means for detecting the infiltration of air. For example, a hydrophone in contact with blood in the blood circuit may detect sounds from air bubbles being generated. Another way in which acoustic sensors 142 may be used is to detect sounds from the patient or ambient surroundings. For example, snoring might indicate that the patient has fallen asleep or disturbed breathing might indicate distress. Other input modalities such as video or image data 152 may also be machine-interpreted to yield such indicators. Patient status, in combination with other information, for example heart rate, may change a normal state into an alarm state. That is, a given heart rate may be indicative of nothing if a patient is watching television but may be indicative of physical distress if the patient is sleeping. In an intelligent system, sounds can contribute in many ways to develop a context by which other signals are either interpreted differently or augmented in some ways. The examples are myriad: activity in the patient's vicinity may indicate that others are in attendance, thereby justifying a higher threshold for an alarm status to be generated; the sounds of children may be recognized by an audio recognition engine and used to alert an attendant that children might be at risk or pose a risk to the patient; speech from the patient may be machine-interpreted and used to trigger alarms or other events. Various artificial intelligence techniques may be employed to leverage such inputs.

Fluid sensors 115 may be used to detect blood or other fluids that have leaked from the blood processing system or connections. For example, a collector placed within the housing of the blood processing machine may detect leaks by funneling any leaking blood into a fluid sensor, which may thereafter indicate the presence of fluid by an output signal. The patient heart rate 130 may be output to the controller/classifier 190 as well. As mentioned above, the heart rate 130 may indicate distress, for example, due to hypovolemia due to blood loss. Continuity detectors 120 and bioimpedance sensors 150 may also be used to provide indications of a needle falling out or loss of blood from tissues.

Air sensors 135 are frequently used in blood processing equipment to prevent air emboli and for detecting leaks in the draw portions of a blood circuit. Also, in the commonly assigned pending application "Method and Apparatus for Leak Detection in a Fluid Line," the entirety of which is hereby incorporated by reference as if fully set forth herein in its entirety, air sensors 135 are proposed to be used to detect leaks in other portions of a circuit by intermittently creating negative pressure in otherwise positive-pressure portions of the blood circuit. The latter technique is a highly reliable method of leak detection. Given the gravity of a leak in an extracorporeal blood processing system, however, it is always useful to increase reliability, if possible.

The controller/classifier 190 may also control components of the blood processing system, such as a pump 175, line clamps 160, and flow controllers 180 such as four-way valves. Control of these components may permit the controller/classifier 190 to shut down the system to prevent further loss of blood. In addition, the controller/classifier 190 may be connected to various alarm output devices 165-170, for example an automatic telephone message generator, a flashing light, an audible alarm, etc.

Figure 2:
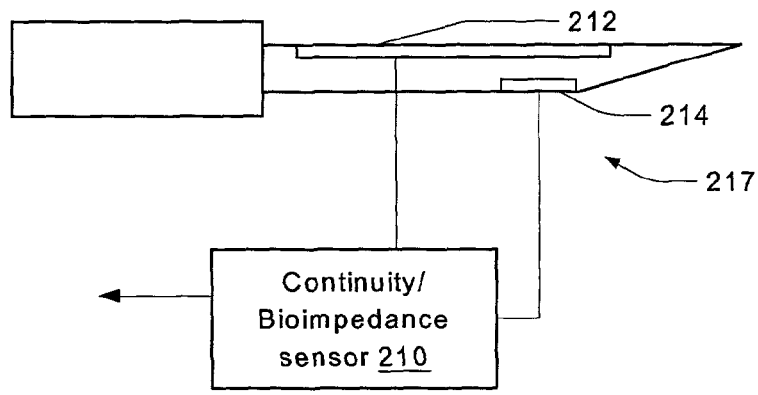
FIG. 2 is figurative illustration of a continuity/bioimpedance sensor built into a hypodermic needle for use with the embodiment of FIGS. 1A-1C as well as other embodiments of the invention.

Referring now to FIG. 2, a hypodermic needle 217, such as might be used to access a fistula or blood vessel of a patient, has pads 212 and 214 for making electrical contact with the patient or blood of the patient. A continuity/bioimpedance sensor 210 provides power and signal processing to generate an output receivable by the controller/classifier 190. One of the contact pads may be elongated and resistive as indicated at 212 so that if the hypodermic needle 217 is drawn out only partly, a graduated signal may be generated. The device of FIG. 2 may, for example, be used to indicate that a needle has fallen out or is beginning to fall out.

Figure 3:
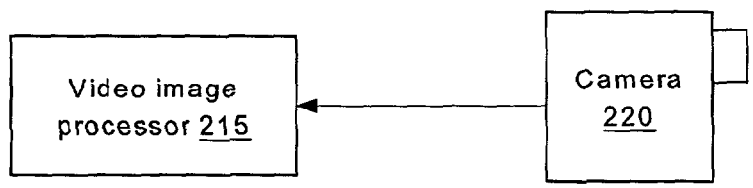
FIG. 3 a figurative illustration of a video image processing front end for use with the embodiment of FIGS. 1A-1C as well as other embodiments of the invention.

Referring to FIGS. 1 and 3, video/image data 152 may be gathered by a camera 220 and pre-processed by a video-image processor 215. The latter may be programmed to recognize physiognomic features of the patient's face, body position, surrounding circumstances, etc. and to generate a classification symbol in response to it. The latter may also be programmed to recognize, by fairly simple image processing, blood pooling on the floor or staining the patient's clothes. The output of video/image processor 215 may be an output vector indicating various states it is programmed to recognize. The video/image processor 215 may be also be a simple device capable only of detecting blobs in the field of view that might indicate blood leaks in the camera's 220 field of view.

Figure 4:
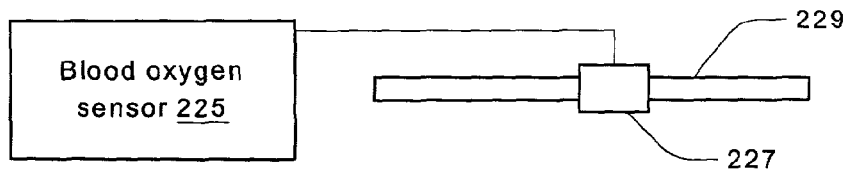
FIG. 4 is a figurative illustration of a blood oxygen sensor for use with the embodiment of FIGS. 1A-1C as well as other embodiments of the invention.

Referring to FIG. 4, a blood oxygen sensor 225/227 (140 in FIG. 1C, shown with a separate sensor part 227 and driver/signal conditioner part 225) may be a simple optical device attached to tubing 229 inside a blood processing system, for example. Blood oxygen may prove a useful metric.

Figure 5:
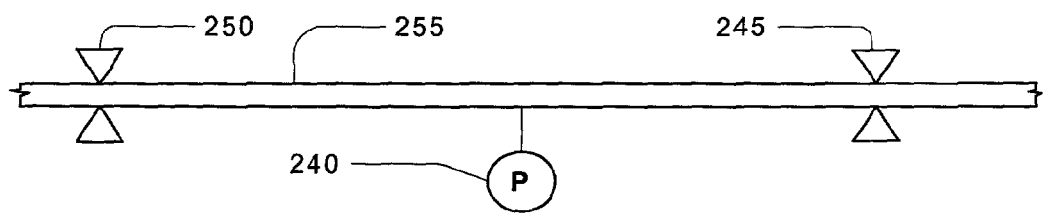
FIG. 5 is an illustration of an intermittent fluid circuit testing apparatus using line clamps and a pressure gauge.

Referring now to FIG. 5, line clamps 245 and 250 may be periodically closed either simultaneously or sequentially so that a positive or negative pressure is built up in a test circuit portion 255. A pressure sensor 240, which may be one of pressure sensors 110 contemplated in the embodiment of FIG. 1, generates a continuous pressure signal which may be received by the controller/classifier 190. If the pressure signal relaxation time constant is inconsistent with a desired integrity of the tested circuit portion, this data may be usable for generating an alarm status, either alone or in combination with other data.

Figure 6:
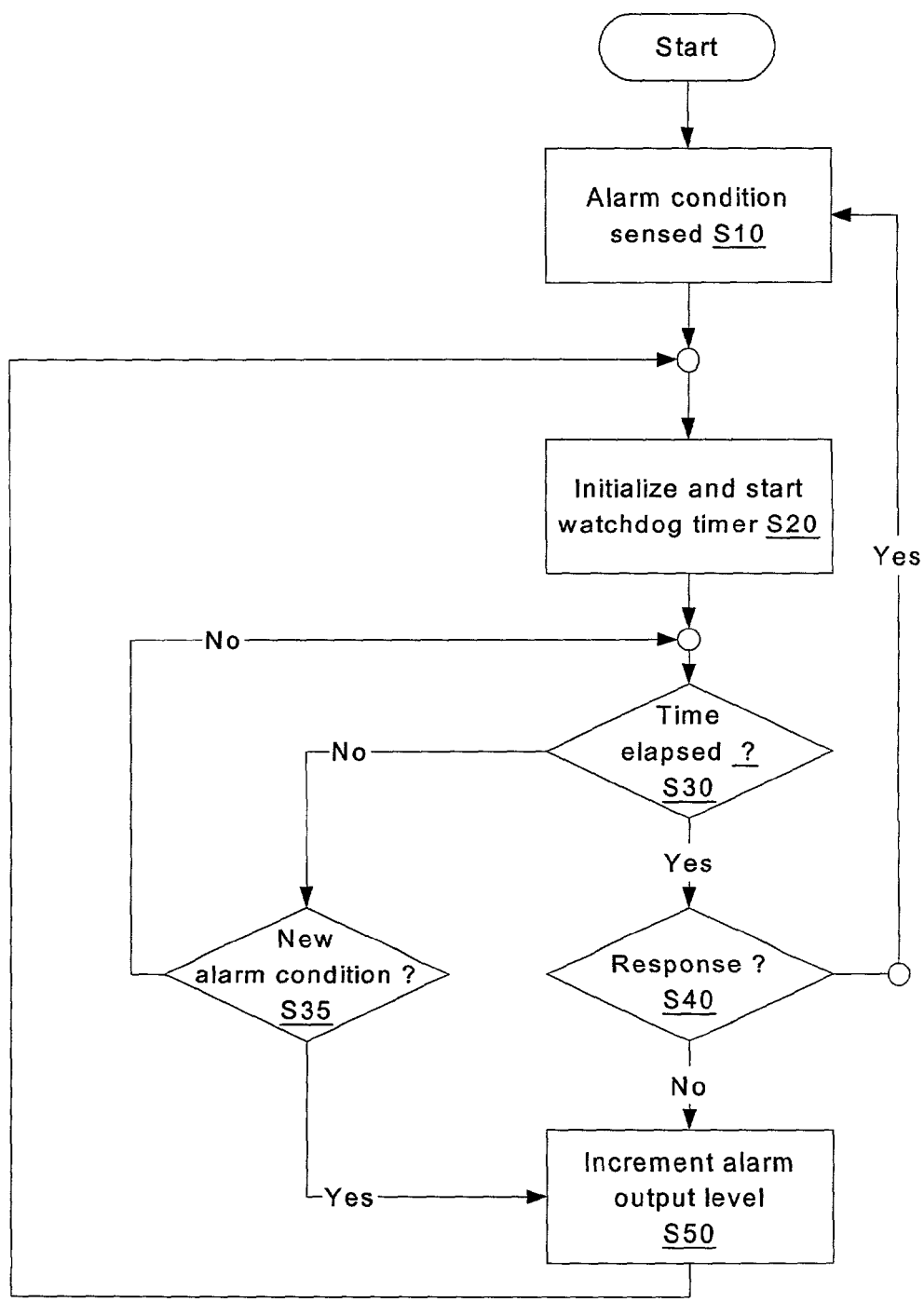
FIG. 6 is a flow chart indicating an alarm status upgrade algorithm according to an embodiment of the invention.

Referring now to FIG. 6, an algorithm that may be used to generate variable alarm states begins with the sensing of an alarm condition in step S10. The alarm condition may be any of the sensors shown in FIG. 1 or others alone or in combination to predict that a leak exists or may exist. In response to the alarm condition, a watchdog timer is initialized and started to count down the time elapsed since the alarm condition event of step S10. Step S30 passes to step S35 as long as the watchdog timer continues to run. Step S35 loops back to step S30 unless a new alarm condition occurs. When the watchdog timer lapses, step S40 determines if the alarm condition has been responded to. If not, an alarm level is incremented in step S50 and control returns to step S20. If a new alarm condition occurs in step S35 before the watchdog timer lapses, control jumps to step S50. If the alarm is responded to in step S40, control returns to step S10 where the system waits for an alarm condition.

Referring now to FIG. 6, an algorithm that may be used to generate variable alarm states begins with the sensing of an alarm condition in step S10. The alarm condition may be any of the sensors shown in FIGS. 1A-1C or others alone or in combination to predict that a leak exists or may exist. In response to the alarm condition, a watchdog timer is initialized and started to count down the time elapsed since the alarm condition event of step S10. Step S30 passes to step S35 as long as the watchdog timer continues to run. Step S35 loops back to step S30 unless a new alarm condition occurs. When the watchdog timer lapses, step S40 determines if the alarm condition has been responded to. Based on a blood flow rate of 500 ml./min., for example, the time interval should be no longer than one minute. Based on a slower potential flow, the interval may preferably be longer. The interval may be adjusted depending on the flow rate of the blood processing machine 310, which may be adjustable. If no response is indicated in step S40, an alarm level is incremented in step S50 and control returns to step S20. If a new alarm condition occurs in step S35 before the watchdog timer lapses, control jumps to step S50. If the alarm is responded to in step S40, control returns to step S10 where the system waits for an alarm condition.

Figure 7:
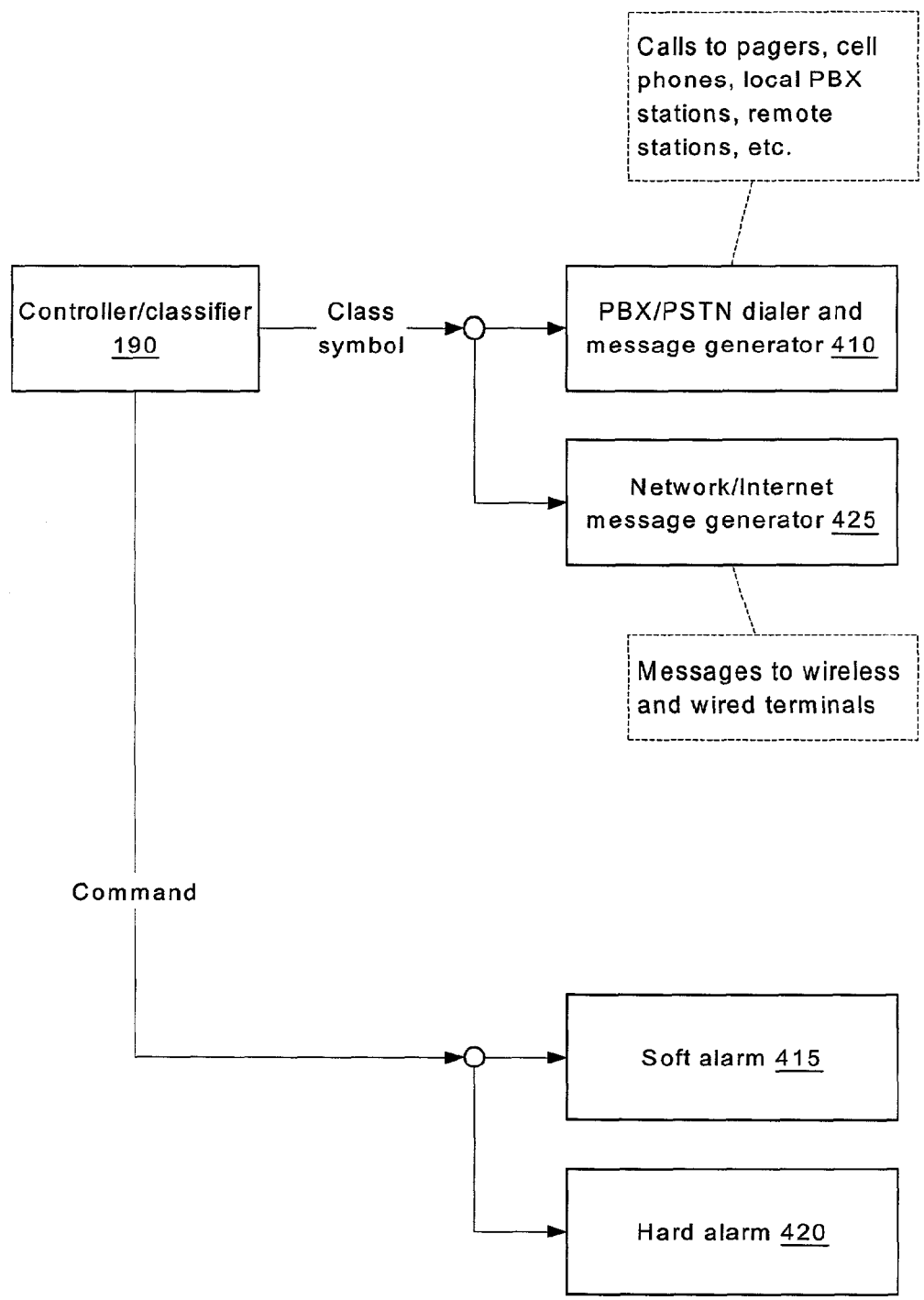
FIG. 7 illustrates functional components of a subsystem for generating multiple alarm-level outputs according to an embodiment of the invention.

Alarms may include messages sent by any suitable messaging system. For example, still referring to FIG. 7, an alarm could be an automated telephone message to a remote location such as a family member or a security station, a doctor's pager or cell phone, or simply a louder alarm signal. All of these may be performed in response to a classification result transmitted as data (here identified as "class symbol") by the controller classifier 190 to a PBX/PSTN dialer and message generator 410. For example, the controller/classifier 190 may send a message by telephone to a caretaker, a doctor, a nurse, or a police-emergency destination. The controller/classifier 190 may also transmit a command symbol along with a class symbol to indicate which of multiple possible channels the message is to be conveyed upon. In addition, the command symbol may include an indication of a type of message based on the current alarm level. Other alarms may employ messages sent via a network or via the Internet, as indicated by a Network/Internet message generator 425 in the figure. These may be programmed to appear as text messages or to sound alarms in other locations.

Note that although the discussion so far has been concerned principally with leak detection, with the multiple inputs available, the system may give notice of various irregular conditions such as patient status, non-leak problems with the blood processing equipment, and others. Therefore, various different types of alarm conditions may be identified besides leaks. Also, each of the different alarm conditions, including leaks, can be further broken down into different types of alarm conditions. Thus, although in the embodiments discussed above, different alarms were distinguished by level, implying a linear scale, the invention is certainly not limited to such a single ladder-type structure. Certain types of alarms may be better suited to certain conditions than others. For example, one type of alarm condition may require the attention of highly skilled person such as a doctor or nurse while another type of alarm condition could be handled by a less-skilled person such as a nurse's aid or orderly. Thus, a message to a doctor's pager might be provided in response to some alarm conditions and not in response to other alarm conditions. To provide for this, as well as the progressive levels of alarm contemplated in the foregoing, separate alarm level "ladders" may be defined. Each ladder may correspond to a different superclass of conditions recognized by the controller/classifier 190. The controller/classifier 190 would then implement alarms according to a current ladder. If multiple alarm conditions arise, these may be handled by following the ladders for both conditions. Thus, messages corresponding to both existing alarm conditions would be generated, for example. For example, a leak detection might cause an audible alarm to be generated at a first level which would progress to a louder alarm which would progress to an alarm at a nurse's station. That would be one ladder. Another ladder might be, for example, a progression from a local alarm (on the processing machine) to a remote alarm (at a nurse's station) to a pager alarm (to a doctor or physician's assistant).

Figure 8:
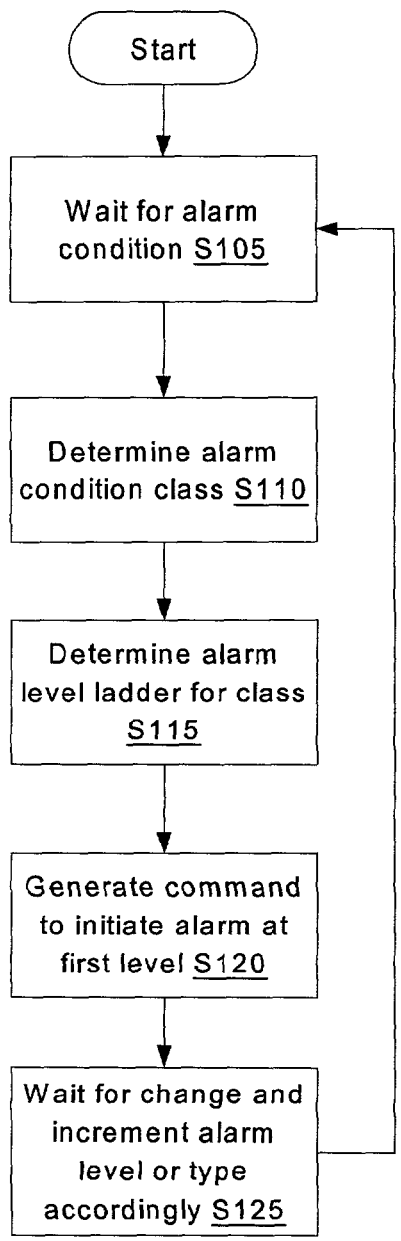
FIG. 8 is a flow chart indicating an alarm status control algorithm which may incorporate the status upgrade algorithm of FIG. 6.

Referring to FIG. 8, a simplified control algorithm for illustrating the above ideas begins with step S105 where the controller/classifier 190 waits for an alarm condition and then determines its alarm class in step S110. In step S115, an alarm level ladder is associated with the alarm condition class identified in step S110. In step S120, a command is generated to invoke the alarm corresponding to the first rung of the ladder selected in step S115. Alternatively, a given ladder may be entered on a higher selected level responsively to a severity of the alarm condition identified in step S110.

Note that although alarm levels were discussed as being incremented responsively to the length of time the condition existed without response thereto, other scaling effects may be used to escalate the alarm level. As discussed above, the alarm condition classification may provide one such scaling factor. Some classes of alarm conditions may be classified as more severe than others. In addition, the severity of a given condition may provide a higher-level entry point or cause the alarm level to escalate. For example, patient distress could be mild, indicating the appropriateness of a first low level alarm, or it could be severe indicating a more urgent alarm should be generated. Again, also, the type of alarm may correspond to the type or severity of alarm condition according to the standards of the system designer.

In step S125, the system may wait for either the severity, type, or delay-till-response warrants an escalation in alarm level or change in the type of alarm. With a response, which resets the alarm condition, control returns to step S105.

Figure 9:
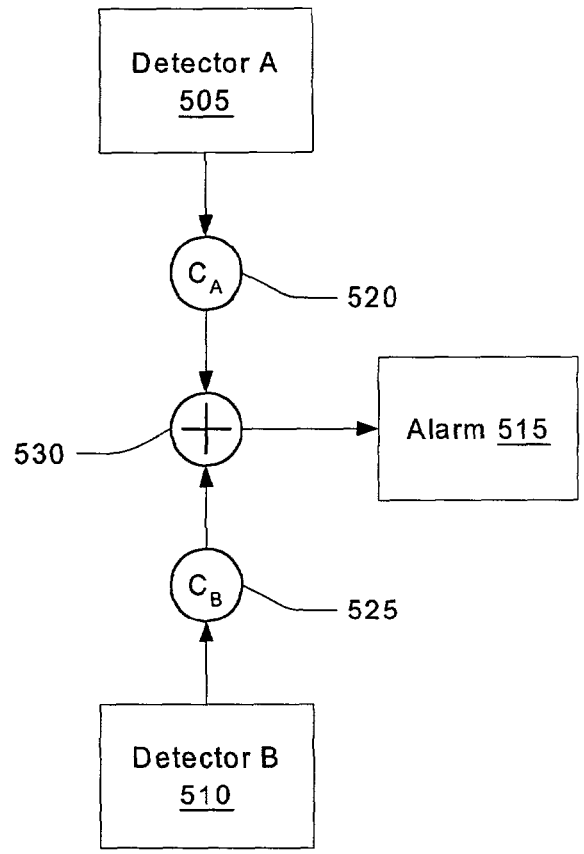
FIG. 9 is an illustration of an analog version of a signal combiner for controlling an alarm output for leak detection.

Note that programmable controllers may be the most versatile and often the cheapest mechanism for implementing aspects of the invention, such as the combination of multiple inputs, they are not the only way. A simple analog system can provide an ability to form a weighted sum of the outputs of two detectors. For example, referring to FIG. 9, Detector A 505 and detector B 510 each applies its respective signal to a respective one of signal multipliers 520 and 525, respectively. The signal multipliers 520 and 525 may amplify the respective signals, including inverting, attenuating, and augmenting its magnitude. A summer 530 adds the amplified values of the two signals to produce a final output that drives an alarm. The result is that one detector's output may function as an inhibitor of another, or it may have the effect of changing the alarm-triggering threshold of the signal from another detector. FIG. 9 is exemplary and not comprehensive. It is possible to use the output of one detector to determine the weight applied to another signal and linear and non-linear combinations of two or more signals may be combined in various ways to extend the combination shown in FIG. 9, as would be clear to a person of skill in the field of complex analog control systems.

Figure 10:
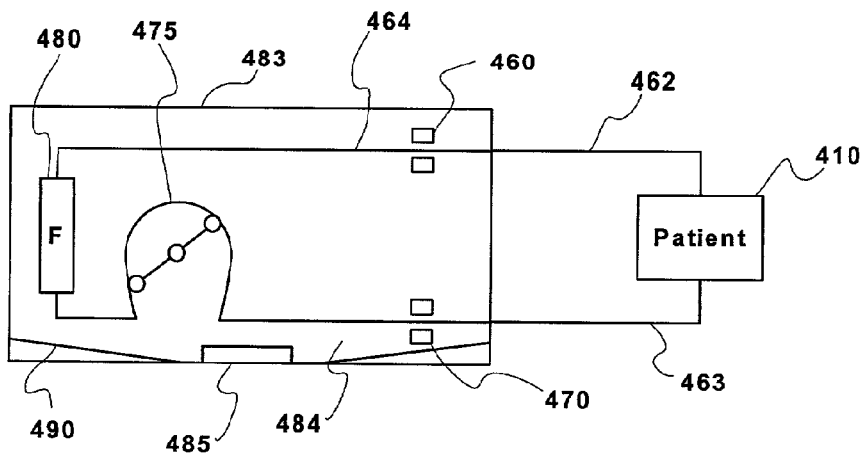
FIG. 10 is an example configuration of a blood processing system with leak detection which combines multiple inputs.

Referring now to FIG. 10, in the area of leak detection, which is one of the most important safeguards involved in extracorporeal blood treatment, an example shows how the "belt and suspenders" approach of combining multiple inputs can be used to clear advantage. A blood processing machine 483 has leak detection components built into it. The machine includes air sensors 460 and 470, a filter 480, and a reversible pump 475, the latter being one mechanism for reversing flow to test the return circuit as discussed in the patent application incorporated by reference above. As discussed in this reference, the two air sensors 460 and 470 may quickly detect any leaks in draw and return accesses 462 and 463 of the patient 410 when the pump is driven in forward and reverse directions, respectively. An additional leak detection feature includes a funnel 490 at the bottom of an enclosure housing a housed portion 484 of a blood circuit 464 with a fluid detector 485 at the bottom of the funnel 490. Any leaks occurring in the housed portion 484 will be directed by the funnel 490 toward the fluid detector 485. The fluid detector 485 may be any suitable device for detecting blood, for example, a continuity tester. The fluid detector 485 may be linked to the same alarm system as the air sensors 460 and 470 and be responded to in the same manner as discussed in connection with any of the embodiments described herein.

The system may be programmed such that the air sensors 460 and 470 "protect" the access lines 462 and 463 outside the machine by providing for flow reversal only as far as necessary to detect leaks in normally-positively pressurized lines. In that case, the fluid detector 485 may provide warning for any leaks inside the blood processing machine 483 and the air sensors protection for the access lines. Alternatively, the system may be programmed such that the protection fields overlap, that is, the pump 475 reverses for a sufficient displacement of blood that any leaks at all may be detected while air detection provides another level of protection. In this case, if the sensitivity of the air detector 460 and 470-based leak detection is raised, but modulated according to the status of the fluid detector 485 signal such that an air sensor signal of a low level indicating a leak does not result in an alarm condition unless it is accompanied by a leak indication by the fluid detector 465, false positives arising from the air sensors can be reduced and the sensitivity of the system enhanced. The sensitivity of the fluid detector may be similarly increased, resulting in the possibility of detecting smaller leaks than a system calibrated to operate without such "cooperation" among leak detection subsystems. Note that the overlap in protection zones can be increased by providing one or more additional fluid detectors under the lines or an extension to the funnel 490 to catch fluid leaking from the access lines 462 and 463.

Figure 11:
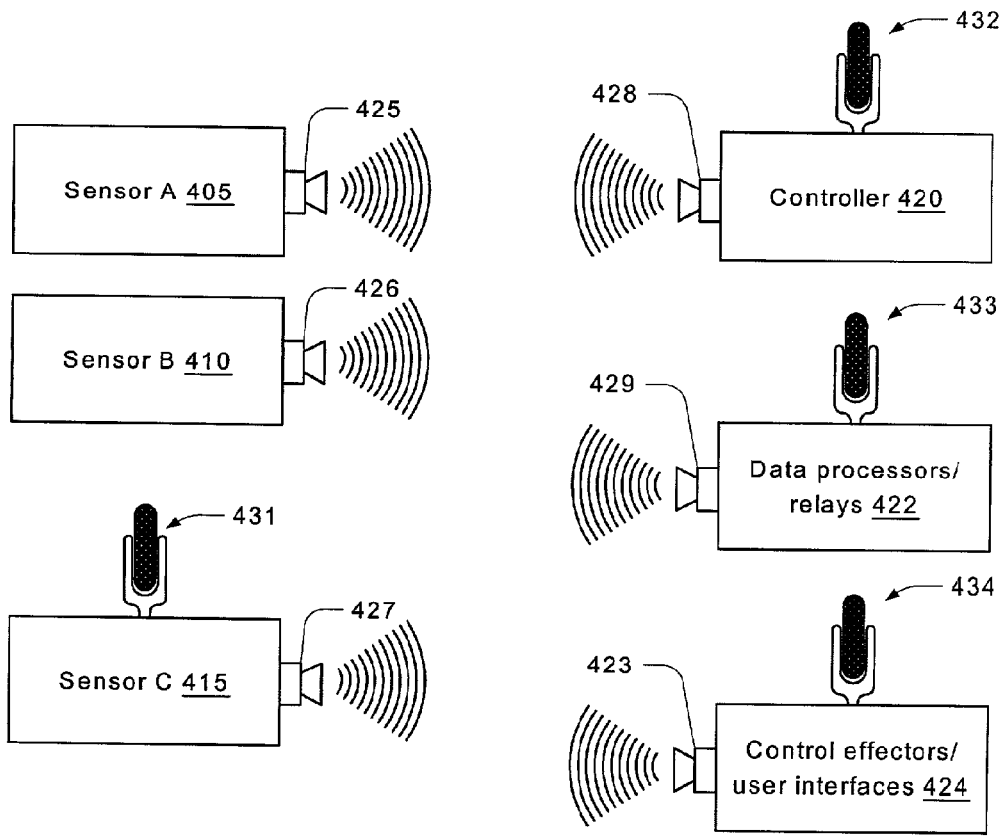
FIG. 11 illustrates components of an alarm network using acoustical signals to communicate among components.

Referring now to FIG. 11, a multiple-input/multiple-level alarm system employs many sensors 405, 410, . . . 415 to communicate with a controller 420 and for the controller 420 to communicate with multiple output devices and user interfaces 424 and data processors and relays 422. In the present embodiment, rather than wire the components together, they communicate with each other using respective sound signal generators 425, 426, 427, 428, 429, and 423 and receivers 431, 432, 433, and 434.

The signals are preferably articulated sufficiently to encode unique identifiers so that multiple systems within "hearing" range of one another do not cause interference. Also, the sound pattern may encode information other than an identifier of the transmitter and/or receiver, for example, it can encode a type of status or magnitude of a detected condition, such as heart rate or degree of wetting of a fluid detector. The sounds may be above or below the frequency range of human hearing to avoid the subjective impact. Alternatively, the signals may be spread over ranges of frequency by modulating with a pseudorandom code. The subject effect of such spread-spectrum signals can be very low due to the noise-like nature of the sound and the low power levels required for data transmission.

In a system where the components of a multiple input, multiple-level alarm system may only need to communicate with each when conditions reach an abnormal status, the audibility of a given signal may pose a problem. The particular alarm system application, therefore, may provide an inoffensive context for using acoustic signals to communicate between components; a sort of "chirp network" to interconnect the functional components of the system. In fact, the audibility of communication signals may provide a benefit. For example, an attendant called to a location by a remote-station alarm may be greeted not only by a user interface indicating the nature of the problem but also by the sending unit's characteristic audio signal. This may reinforce the output from the user interface increasing comprehension by the attendant of the alarm condition that occurred.

Some sensors, such as indicated for sensor C 415, may have the ability to receive as well as send signals. The data processor/relay 422 may be, for example, a component of the acoustic network that processes information outside the controller 420. For example, it could reduce data from other sources unburdening the controller 420 or permitting feature-upgrades to the controller without requiring its replacement or modification.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A leak detection device for detecting a leak in an extracorporeal blood treatment machine, comprising:
a first detector outputting a first detection signal;
a second detector outputting a second detection signal;

a signal combiner connected to said first detector and said second detector to form a combination signal responsive to both said first and second detection signals to generate an alarm output for transmission to an alarm device;

said first detector being adapted to detect a first condition that is correlated with a probability of a leak in a blood circuit;

said second detector being adapted to detect a second condition that is correlated with a probability of a leak in said blood circuit, wherein said first detector includes an image classifier connected to a camera oriented to image a patient, and wherein said second detector includes at least one of a detector of air in said blood circuit, a detector of fluid outside said blood circuit, a detector of pressure in said blood circuit, an image classifier connected to a camera oriented to image a patient, or a device to measure a patient heart rate, blood oxygen level or the tissue bio-impedance of the patient.

2. A device as in claim 1, wherein said signal combiner includes a network classifier.

* * * * *